United States Patent [19]

Kotani et al.

[11] Patent Number: 4,816,132
[45] Date of Patent: Mar. 28, 1989

[54] SHEET TYPE ELECTRODE

[75] Inventors: Haruo Kotani; Katsuhiko Tomita; Takaaki Yada; Tsuyoshi Nakanishi, all of Miyanohigaski, Japan

[73] Assignee: Horiba, Ltd., Kyoto, Japan

[21] Appl. No.: 124,567

[22] Filed: Nov. 24, 1987

[30] Foreign Application Priority Data

Nov. 27, 1986 [JP] Japan .................. 61-283802
Nov. 28, 1986 [JP] Japan .................. 61-285371

[51] Int. Cl.⁴ ........................................... G01N 27/36
[52] U.S. Cl. ..................... 204/408; 204/414; 204/420; 204/435
[58] Field of Search .............. 204/420, 414, 435, 408

[56] References Cited

U.S. PATENT DOCUMENTS

| 3,833,495 | 9/1974 | Grubb | 204/414 |
|---|---|---|---|
| 3,911,901 | 10/1975 | Niedrach et al. | 204/414 X |
| 3,957,612 | 5/1976 | Niedrach et al. | 204/414 |
| 4,053,381 | 10/1977 | Hamblen et al. | 204/416 |
| 4,105,509 | 8/1978 | Jungck | 204/1 T |
| 4,133,735 | 1/1979 | Afromowitz et al. | 204/420 X |
| 4,280,889 | 7/1981 | Szonntagh | 204/420 X |
| 4,282,079 | 8/1981 | Chang et al. | 204/435 X |
| 4,454,007 | 6/1984 | Pace | 204/1 T |
| 4,468,271 | 8/1984 | Pierson | 204/420 X |
| 4,592,824 | 6/1986 | Smith et al. | 204/416 |

Primary Examiner—G. L. Kaplan
Attorney, Agent, or Firm—Price, Gess & Ubell

[57] ABSTRACT

A flat shaped composite electrode includes a flat substrate having a high electrical insulating property. A flat inside pair of electrodes and a flat outside pair of electrodes are fixed on the substrate. A flat support layer having a high electrical insulating property overlays the electrodes and substrate. The support layer describes two holes into which a gelatinized internal solution is placed. An ion response glass membrane is mounted on the support layer and over one hole, while a liquid junction membrane is similarly mounted over the other hole.

14 Claims, 4 Drawing Sheets

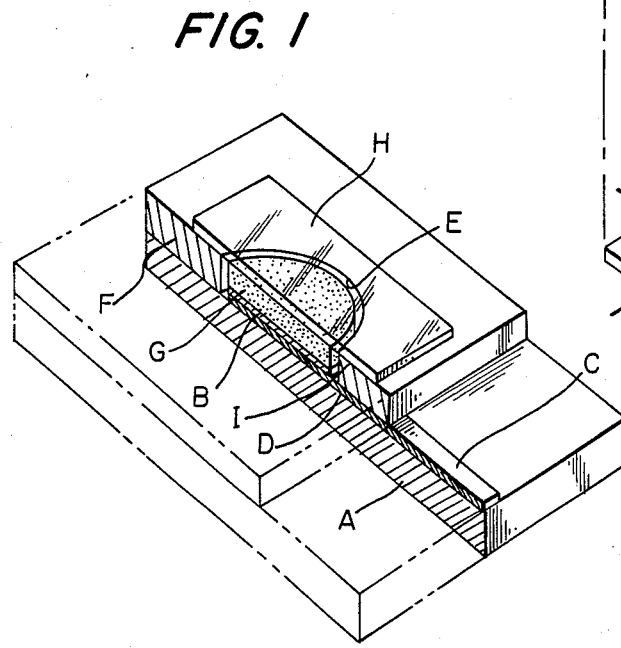
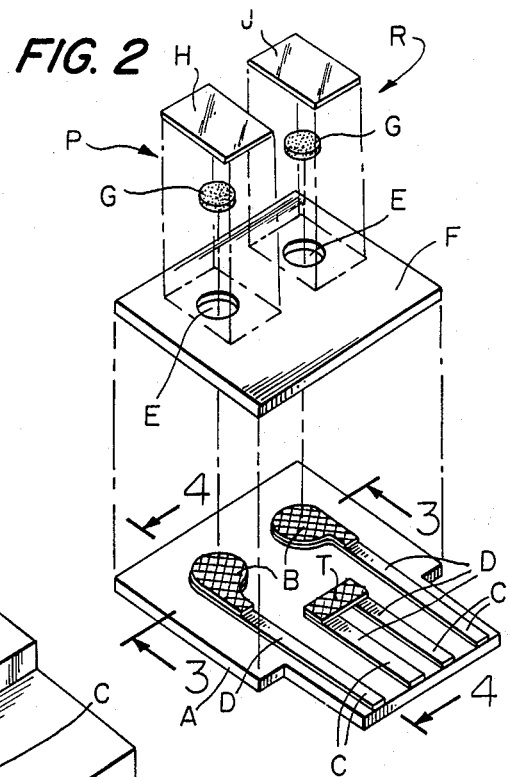
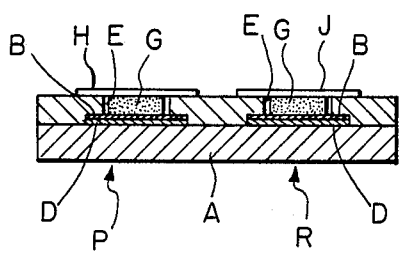
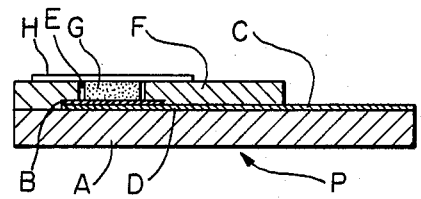
FIG. 1
FIG. 2
FIG. 3
FIG. 4

SHEET TYPE ELECTRODE

BACKGROUND OF THE INVENTION

1. Field of the Invention

The present invention relates generally to ion concentration measuring electrodes and, more specifically, to a sheet type electrode for measuring pH, pNa and the like, and methods for making the same.

2. Description of the Prior Art

A conventional electrode for measuring ions, such as pH and pNa, has been generally called a glass electrode and is shown in FIG. 12. The glass electrode comprises a support tube "a" formed of electrically insulating glass; a semi-spherical ion-response glass membrane "b" responsive to ions, such as pH and pNa, which is formed by the balloon method and joined to a pointed end of the support tube "a"; an internal electrode "c"; and an internal solution "d" enclosed in the support tube "a".

However, the above described ion-measuring electrode (glass electrode) having the conventional construction exhibits disadvantages. For example, since its ion-response glass membrane "b" must be formed by the balloon method, an adjustment of fire and blowing for adjusting a film thickness during its processing, or the prevention of microcracks which can be generated when the ion-response glass membrane "b" is joined to the support tube "a", require a considerable amount of skill in the art. Also, since it is difficult to mass-produce, not only is the cost of production remarkably high but also its construction cannot be other than large-sized, and its operation, maintenance and the like are also unsatisfactory.

As to the glass electrode having the conventional construction as shown in the above described FIG. 12, the semi-spherical ion-response glass membrane "b" having a film thickness (0.1 to 0.3 mm) could, for example, be realized by the balloon method even though it requires a considerable amount of skill in the art. In the event that the present invention of a sheet type glass electrode is sought to be produced, an ion-response super-thin glass membrane, such as pH-response glass membrane, is indispensable. The membrane must be flat and plate-like, and requires a film thickness near the limit of glassification. Such a membrane cannot be produced at the present, and thus the pending present invention of a sheet type glass electrode has not been realized.

That is to say, a thin plate glass having a thickness of at least about 1 mm has been produced by the vertical pulling-up method. A plate glass having a thickness less than the above described thickness (using, for example, a preparat and the like) has been produced by additionally subjecting the vertically pulled plate glass to a polishing process. However, in that case, not only is the cost of production remarkably increased but also relatively large uneven portions and cracks remain on the glass surface, and the resulting thin plate glass cannot be used as a glass-response membrane in an ion-concentration measuring electrode. Because of the large, uneven portions and microcracks in the plate glass, smooth absorption and desorption of the sample solution on and from the glass surface cannot be achieved, whereby accurate measurements cannot be achieved.

In addition, a prior method of producing a super-thin, flat plate glass includes a part of a circumferential surface of a super-thin, semi-spherical glass formed by the balloon method which is cut off and then reformed as a flat plate glass by means of a hot plate press. A prior art preformation method has also been used in which a previously molded glass is heated up to temperatures higher than a softening temperature to extend the glass. In the case of the former glass-reforming method, disadvantages occur in that a sufficiently large super-thin, flat plate glass is difficult to obtain and microcracks are apt to be generated. In the case of the latter preformation method, disadvantages occur in that a remarkably large-scale apparatus is required for production and a strain is apt to remain in the finished super-thin, flat plate glass. Moreover, both the above described methods exhibit a temperature-viscosity curve having a relatively gentle slope and they are effective merely for a normal glass (so called sodium glass) having a composition of a relatively wide melting temperature range. In the case where the above described methods are applied to a special glass (so called lithium glass) exhibiting a temperature-viscosity curve having a relatively steep slope and having a composition in which the melting temperature range is narrow, crystallization (detransparency) of the glass occurs, whereby it is quite impossible to obtain the desired super-thin, flat plate glass.

In addition, to realize a sufficiently reliable sheet type glass electrode, there is a problem in that a high electrical insulator must be secured between the flat, plate-like, ion-response glass membrane and a support layer and a substrate, as well as realizing the above described flat plate-like ion-response glass membrane itself.

The above described problem is also present in a composite electrode in which a glass electrode is integrated with a reference electrode.

The present invention was achieved in view of the above described state of the prior art and it is an object of the present invention to overcome the above described problems, whereby the present invention is a remarkably compact sheet type electrode which is superior in reliability, operation and maintenance, and can be easily and inexpensively produced.

SUMMARY OF THE INVENTION

A sheet type composite electrode according to the present invention is characterized by a glass electrode and a reference electrode placed side by side under the condition that they are opened toward an upper surface side, and in combination provide a sheet type shape as a whole.

And a sheet type glass electrode according to the present invention is characterized by a substrate A formed of a material having a sufficiently high electrical insulating property, an electrode D provided with an internal electrode portion B on the upper surface of the substrate A, a lead portion C stuck to an upper surface of the substrate A, and a support layer F formed of a material having a sufficiently high electrical insulating property and provided with a hole E at a place corresponding to the internal electrode portion B. Thereby, the lead portion C and its circumference are exposed. Additionally, the hole E in the support layer F is filled with a gelatinized internal solution G. A flat, plate-like ion-response glass membrane H, which is produced by subjecting a predetermined sized, super-thin, flat, plate-like glass to a high-speed surface heating treatment after being previously heated, is fixedly mounted on the upper surface of the support layer F and over the hole E. The membrane H is mounted by the use of adhesives I having a sufficiently high electrical insulating property so that a lower surface thereof may be closely fixed to an upper surface of the gelatinized internal solution G and the hole E may be tightly filled with the gelatinized internal solution G, as shown in FIG. 1.

Furthermore, a method of manufacturing a super-thin flat plate glass, according to the present invention, is characterized by producing a first glass sheet having an aimed thickness, or, where it is impossible to produce the first glass sheet having the aimed thickness, having a thickness near to the aimed thickness by slicing, with mechanical cutting means, a glass block to provide an appointed composition. A resulting surface of the first glass sheet is subjected to an etching treatment to produce a second glass sheet having the aimed thickness in the event that the first glass sheet has a thickness larger than the aimed thickness. An appointed quantity of thermal energy is added to a surface of the first glass sheet or the second glass sheet within a short period of time and under the condition that the first or second glass sheet was previously heated at a temperature just lower than its melting temperature as a whole, whereby only the surface of the first or second glass sheet is melted and then solidified.

BRIEF DESCRIPTION OF THE DRAWINGS

FIG. 1 is a partially sectioned, perspective view of a basic construction of a sheet type glass electrode according to the present invention.

Figure 5:
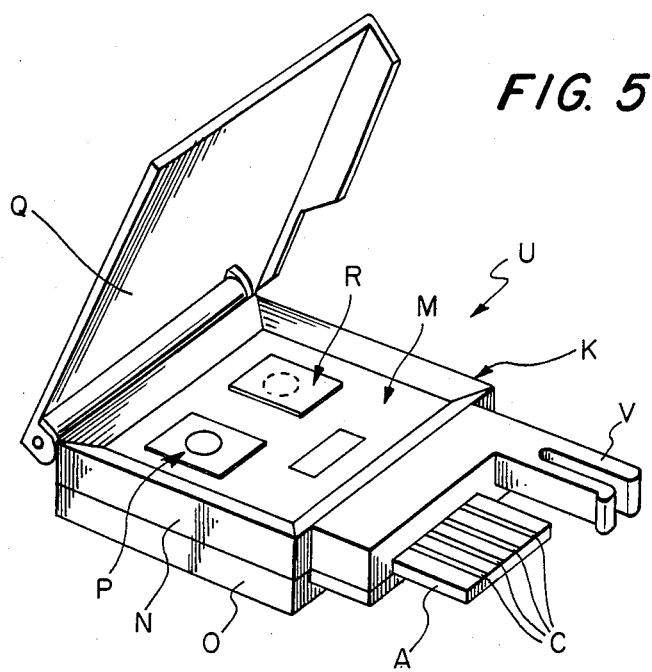
Figure 6:
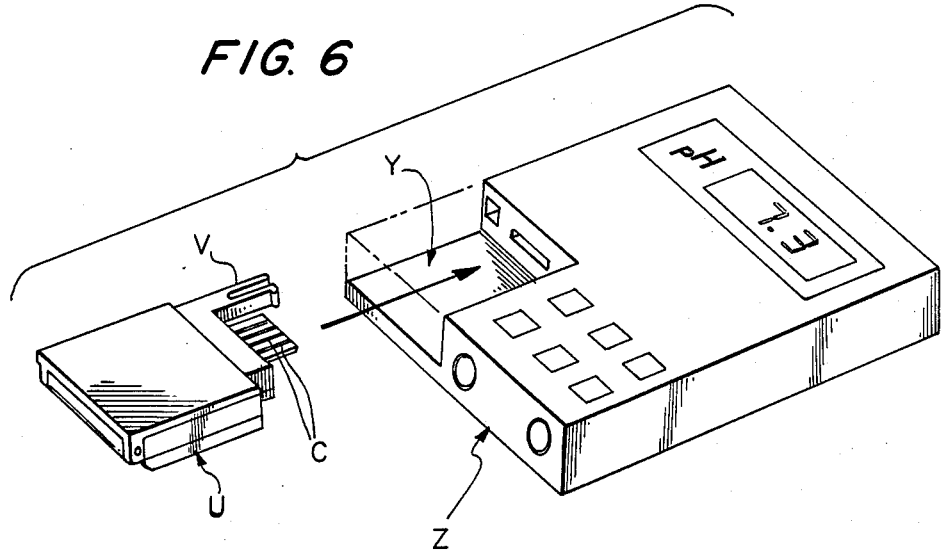

In addition, a construction of a pH-measuring sheet type composite electrode as a preferred embodiment of a sheet type glass electrode according to the present invention is shown in FIGS. 2 to 6, in which:

FIG. 2 is an exploded, perspective view;

FIG. 3 is a view taken along the line III—III of FIG. 2;

FIG. 4 is a view taken along the line IV—IV of FIG. 2;

FIG. 5 is a perspective view of a pH unit having a housing and a pH-measuring sheet type composite electrode therein; and FIG. 6 is a perspective view showing a connection of the pH unit with a measuring device body.

Figure 7:
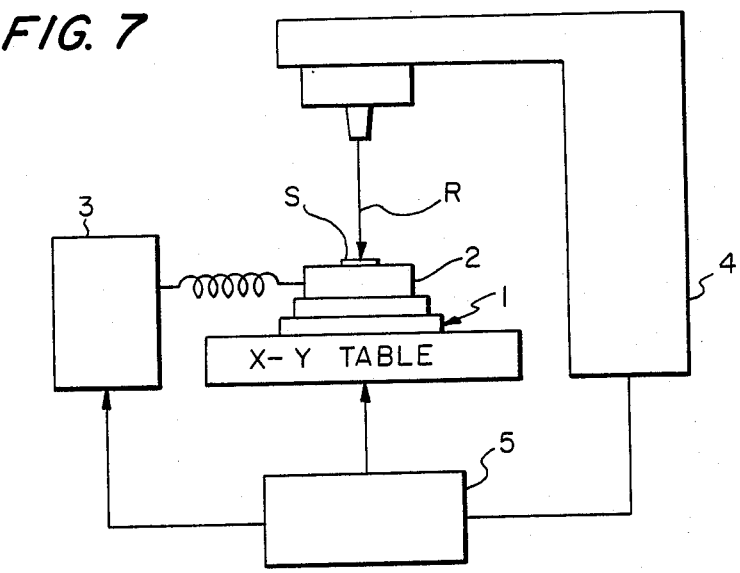
Figure 8:
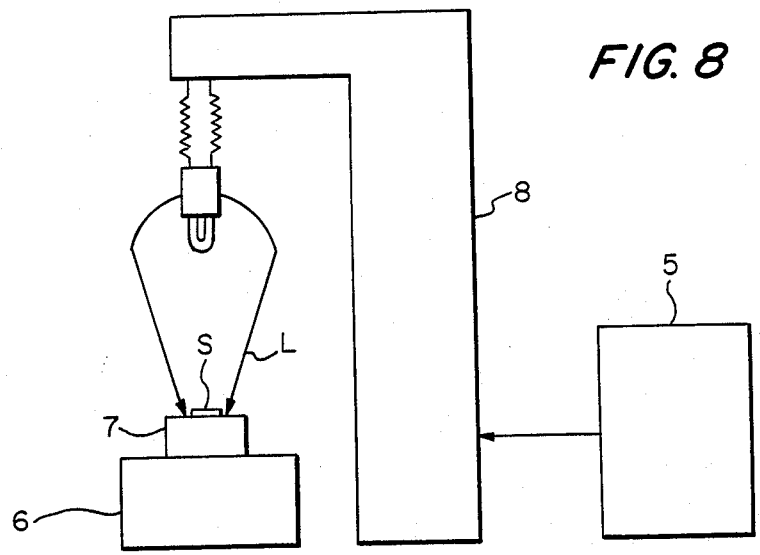
Figure 9:
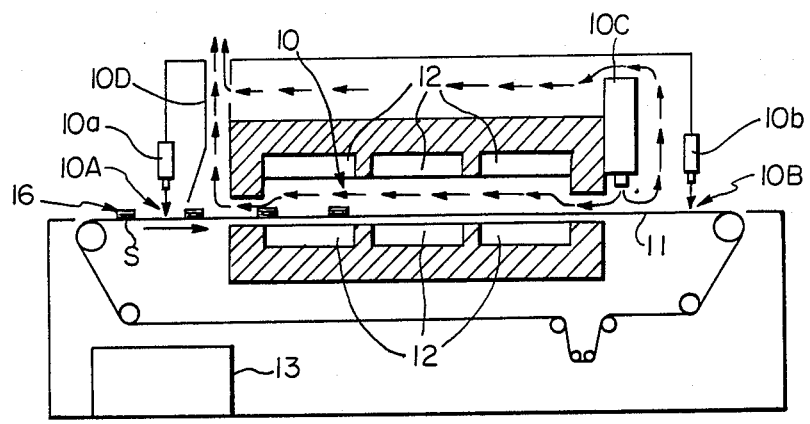
Figure 10:
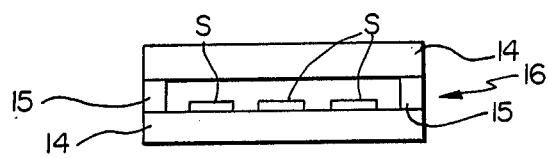
Figure 11:
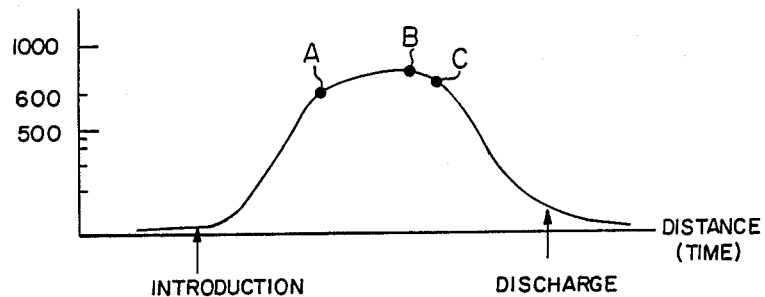

Furthermore, a procedure of producing a flat, plate-like, ion-response glass membrane as a main constituent member of a pH unit is shown in FIGS. 7 to 11, in which:

FIG. 7 is a schematic diagram showing a system of a first method;

FIG. 8 is a schematic diagram showing a system of a second method;

FIG. 9 is a schematic diagram showing a system of a third method;

FIG. 10 is a partial, side view showing principal parts in the system of the third method; and FIG. 11 is a graph showing an example of control characteristics of the system of the third method.

Figure 12:
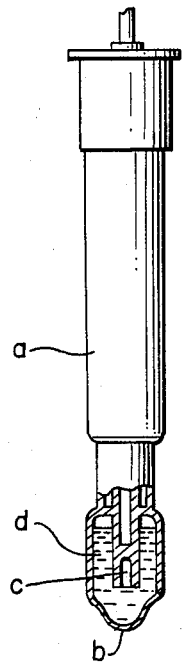

And, the technical background of the present invention and the problems of the prior arts are described with reference to FIG. 12, in which:

FIG. 12 is a partially sectioned side view showing an ion-measuring glass electrode having a conventional construction.

DESCRIPTION OF THE PREFERRED EMBODIMENTS

The preferred embodiments of the present invention are below described with reference to the drawings (FIG. 2 to FIG. 11). First, a sheet type electrode for use in the measurement of pH is illustrated. FIG. 2, which is an exploded perspective view; FIG. 3, which is a section view of FIG. 2 taken along a line III—III thereof; and FIG. 4, which is a sectional view of FIG. 2 taken along a line IV—IV thereof, show a sheet type composite electrode for use in the measurement of pH according to a preferred embodiment of the present invention.

Referring to FIGS. 2 to 4, reference mark A designates a substrate formed of materials (in the present preferred embodiment, a polyethylene terephthalate plate) having a sufficiently high electrical insulating property even when immersed in a solution including electrolytes. The substrate A includes organic high molecular materials, for example polyethylene, polypropylene, polyethylene terephthalate, acryl, polyfluoroethylene and the like. It also includes inorganic materials, for example, silica glass, pyrex glass and the like.

Two pairs of electrodes D (an inside pair of electrodes and an outside pair of electrodes) are provided on the substrate A and are formed by sticking a metal to an upper surface of the substrate A. The metal is selected from a group consisting of electrically conductive Ag, Cu, Au, Pt and the like, alloys thereof and the like, or a paste including said metal, or a semiconductor, such as $IrO_2$ and $SnO_2$. The electrodes D are formed by a physical plating method, such as a vacuum deposition method and a CVD method; or a chemical plating method, such as an electrolytic method and a non-electrolytic method; or a printing method, such as a silk screen method, anastatic printing and flat plate printing. In the present preferred embodiment, the upper surface of the substrate A is subjected to a graft processing and an anchoring process by a silane coupling agent and the like. Then, an Ag paste is printed on the upper surface of the substrate A by the silk screen printing method.

In addition, a base end portion, which is formed as a lead portion C, is provided in every electrode D and is positioned at one end or edge portion of the substrate A. The other pointed end portions of the outside pair of electrodes D, D are nearly circular and positioned at a nearly central portion of the substrate A. Those end portions are formed as the internal electrode portions B, B and are coated with an electrode material, such as AgCl, by physical plating methods, chemical plating methods, or printing methods in the same manner as above described.

A temperature-compensating electrode portion T is provided and extends over and between the other pointed end portions of the inside pair of electrodes D, D. The portion T is positioned at a nearly central portion of the substrate A. For example, a thermistor and the like are used as the temperature-compensating electrode portion T.

The substrate A is provided with a support layer F which is formed of a material having a sufficiently high electrical insulating property in the same manner as the substrate A and is provided with holes E, E. The placement of the holes E, E correspond to both of the internal electrode portions B, B (in the present preferred embodiment, a polyethylene terephthalate layer) formed on the upper surface of the substrate A by, for example, the screen printing method or a hot melting means using adhesives (for example, polyolefine series adhesives, silicon resin series adhesives and the like). Consequently, all of the lead portions C and their circumferences are exposed. The support layer F is then capable of securing a sufficiently high electrical insulating property (for example 10 MΩ or more). Also, the upper surface of the support layer F is subjected to a grafting process and an anchoring process by means of a silane coupling agent and the like.

In addition, both holes E, E of the support layer F are filled with disc-like gelatinized internal solutions G, G. The solutions G, G are formed by adding a gelatinizer (for example, agar-agar, gelatine, glue, alginic acid, various kinds of acrylic water-absorbing polymer and the like) and a gel-evaporation inhibitor (for example, glycerine, ethylene glycol and the like) to a basic internal solution (for example, obtained by adding a phosphoric acid buffer solution to a 3.3 M-aqueous solution of KCl supersaturated with AgCl). Such mixture is, for example, heated to turn into a paste and then printed by the screen printing method and the like so that the upper surface of the disc-like gelatinized internal solutions G, G may be slightly projected over the upper surface of the support layer F, and the disc-like gelatinized internal solutions G, G overlap the internal electrode portions B, B.

Above the gelatinized internal solution G in a first hole E is a flat, plate-like pH-response glass membrane H. The membrane H is produced by subjecting a flat, plate-like, super-thin glass (previously formed with an appointed size) to a high-speed surface heating treatment after being previously heated. The heat treated glass membrane H is then fixedly mounted on the upper surface of the support layer F and over the first hole E. The glass is so mounted by the use of adhesives I having a sufficiently high electrical insulating property (for example, organic high molecular adhesives, such as silicon series adhesives, epoxy series adhesives, urethane series adhesives and the like, containing a silane coupling agent and the like). The lower surface of the flat, plate-like pH-response glass membrane H thereby contacts the upper surface of the gelatinized internal solution G and the gelatinized internal solution G may be tightly sealed in the hole E to form a pH-measuring glass electrode P.

Above the gelatinized internal solution G in the other or second hole E is a liquid junction membrane J which is formed of inorganic sintered porous materials, organic high molecular porous materials or the like impregnated with KCl. The membrane J is fixedly mounted on the upper surface of the support layer F and over the second hole E so that the lower surface of the liquid junction membrane J contacts the upper surface of the gelatinized internal solution G to form a reference electrode R.

A pH-measuring sheet type composite electrode constructed in the above described manner has a thickness of about 0.5 mm as a whole in the present preferred embodiment and is housed in a casing K made of synthetic resins. The casing K is configured so that the pH-measuring glass electrode P and the reference electrode R may be opened to expose the upper surface side and one edge portion of the electrodes, i.e., where the lead portions are formed. The casing K is further configured so that the pH-measuring glass electrode P and the reference electrode R protrude toward the outside of the casing K to form a tip-like measuring electrode unit U.

The casing K includes an upper frame member N forming an indented portion M, into which the sample solution is poured, a bottom cover O of the upper frame member N, and an upper cover Q, which is swingably and closably mounted on one end edge portion of the upper frame member N, which provides the indented portion M. In addition, the casing K (in the present preferred embodiment, a portion of the upper frame member N) is provided with an engaging projection V for insertion into a measuring device body Z, which will be described later. The engaging projection V connectedly projects from an end edge of a side from which the lead portions C extend.

With the tip-like measuring electrode unit U, including the pH-measuring sheet type composite electrode having the above described construction, a sample solution of one drop to several drops is poured into the indented portion M after opening the upper cover A that brings the pH-measuring glass electrode P and the reference electrode R, which are positioned on a bottom portion of the indented portion M, into sufficient contact with the sample solution and then the upper cover Q is closed. Subsequently, the tip-like measuring electrode unit U is inserted into a fitting portion Y of the measuring device body Z which is constructed in the form of a card type bench electronic calculator at the lead portions C. The projection V becomes engaged to then measure pH of the sample solution.

Next, the procedure of a very novel method of producing the pH-response glass membrane H (10 mm deep, 8 mm wide, and 0.1 mm thick in the present preferred embodiment) and a pNa-response glass membrane and the like will be described in detail.

First, appointed quantities of the appointed powdery ingredients (such as found in conventional glass membranes of glass electrodes) are blended and the resulting mixture is melted in a platinum crucible and the like and then solidified. Subsequently, the solidified mixture is subjected to an annealing treatment to produce a large-sized glass ingot having the appointed composition (for example, pH-glass). Thus, a large-sized glass ingot of 328 mm deep, 93 mm wide, and 23 mm thick is obtained in the present preferred embodiment.

If the large-sized glass ingot is produced in such a manner, advantages occur in that not only is the cost of production considerably reduced but also stabilized quality and uniform composition can be obtained.

Then, the above described large-sized glass ingot is cut into suitably-sized glass blocks by means of a mechanical cutting means (for example, comparatively easy and practical means, such as a wire-cutting method, an inside circumference blade cutting method, and an outside circumference blade cutting method). Thus, fourteen pieces of glass block of 45 mm deep, 45 mm wide, and 23 mm thick can be obtained in the present preferred embodiment.

Subsequently, each of the resulting glass blocks is sliced by means of a mechanical cutting means, similar to those above, to produce a first glass sheet having a thickness (0.2 mm) or as near as possible to an aimed thickness (0.1 mm). Thus, the first glass sheet of 45 mm deep, 45 mm wide, and 0.2 mm thick is obtained in large numbers.

However, since each first glass sheet has a thickness (0.2 mm), which is still larger than the aimed thickness (0.1 mm), and leaves a comparatively large unevenness due to said mechanical cutting on a surface thereof, it is still opaque (frosted glass-like). Accordingly, it cannot yet be used as the pH-response glass membrane H.

So, each first glass sheet is immersed, for example, in a 5%-aqueous solution of NH₄F and the like. The surfaces (both the right side and the back side) of the first glass sheet are further subjected to an etching treatment to etch off an appointed thickness (0.05 mm in the present preferred embodiment) and to produce a second glass sheet having the aimed thickness (0.1 mm) and a slight reduction in surface unevenness. Although this etching treatment leads to the possibility of obtaining the second glass sheet having a more reduced thickness and more reduced surface unevenness, it is still semi-transparent. That is to say, it is not yet in a completed condition. Thus, the second glass sheet of 45 mm deep, 45 mm wide, and 0.1 mm thick in the present preferred embodiment.

In addition, in the event that the glass block is cut to obtain the glass sheet and the first glass sheet has the aimed thickness, the process of producing the second glass sheet by etching is not required.

Subsequently, each second glass sheet is divided by a mechanical cutting means (dying by means of scriber and the like) into a tip-like second glass sheet having an appointed size. The preferred appointed size and thickness are 10 mm deep, 8 mm wide, and 0.1 mm thick.

In addition, this tip-like second glass sheet is sufficiently washed, for example, by ultrasonic washing and the like to remove waxes, fluorine or the like.

It is necessary to eliminate the unevenness remaining on a surface of each tip-like second glass sheet obtained in the above described manner to give a transparent and sufficiently flat surface. To do so, the tip-like second glass sheet is subjected to the following novel surface heat treatment.

The novel heat treatment effectively prevents crack generation and melting condensation due to the generation of a sudden temperature change or a remarkably heterogeneous temperature distribution which have been a remarkably difficult problem in the heat treatment of glass. First, the tip-like second glass sheet is heated up to temperatures immediately before its melting temperature as a whole and then, under such heated condition immediately before its melting, an additional appointed quantity of thermal energy is added to the surface of the heated tip-like second glass sheet within a short period of time, whereby only the surface is melted and then solidified. That is to say, the tip-like second glass sheet is subjected to high-speed surface heat treatment with previous heating.

As a result, a super-thin, flat plate glass, meeting the severe requirements of having a sufficient size, generating no microcracks, strain or crystallization (detransparency), giving a sufficiently flat and transparent surface, and capable of being sufficiently used as a pH-response glass membrane H, can be easily and inexpensively produced regardless of its composition.

Although various kinds of methods are thought of as concrete means for carrying out the high-speed surface heat treatment with previous heating, the test experiments indicated that the following three methods were most suitable.

One of them (the first method) is "the laser heat radiation method with previous heating" (FIG. 7). Such method utilizes an XY table 1, a heater block 2 placed on the XY table 1, a temperature regulator 3 for the heater block 2, a laser radiating apparatus 4 capable of radiating, for example, a $CO_2$ laser R (several watts to about 10 watts are sufficient) onto an appointed point on the XY table 1, and a controller 5 for controlling the XY table 1.

The tip-like second glass sheet S obtained in the above described manner is placed on the heater block 2 and then, at first, the temperature regulator 3 for the heater block 2 is controlled by means of the controller 5. The tip-like second glass sheet S is subjected to high-speed surface heat treatment with previous heating, in which the tip-like second glass sheet S is first heated up to temperatures (in the present preferred embodiment, at about 600° C. lower than the softening point) immediately lower than the melting temperature. Then, under such previously heated condition, immediately before the melting, the XY table 1 and the laser radiating apparatus 4 are controlled by means of the controller 5 and a $CO_2$ laser R is radiated onto the desired places or all over the surface of the tip-like second glass sheet S on the heater block 2 by scanning the $CO_2$ laser at an appointed speed (in the present preferred embodiment about several cms/sec). The scanning adds an appointed quantity of thermal energy to the tip-like second glass sheet S within a short period of time, whereby only the surface is melted and then solidified.

In addition, generally upon a light incident upon glass, at first the heat absorption occurs on its boundary surface (surface), so that both the right side and the rear side of the tip-like second glass sheet S can be simultaneously treated by merely radiating the $CO_2$ laser onto the one surface side of the tip-like second glass sheet. In addition, this laser heat radiation method with previous heating is particularly suitable where it is sufficient that only a part (or desired place) of the boundary surface of the tip-like second glass sheet S is to be finely glassified.

Another method (the second method) is "the lamp heat radiation method with previous heating" (FIG. 8). Such method or system utilizes a stationary bed 6 formed of an insulating material; a preferably black working board 7 (for example, a carbon plate) formed of a material superior in heat-resistance, conductivity and radiation and placed on the bed 6; a lamp light radiating apparatus 8 (for example, a halogen lamp light) capable of collecting a lamp light L onto the working board 7, adjusting a luminous output, a collecting degree, a radiation time and the like, and obtaining a sufficient luminous output (a maximum of a thousand and several hundred degrees at centigrade can be realized in the collection portion); and a controller 5 for controlling the lamp light radiating apparatus 8.

The tip-like second glass sheet S, which is obtained in the above described manner, is placed on the working board 7 and then subjected to high-speed surface heat treatment with previous heating, in which the lamp light radiating apparatus 8 is controlled by means of the controller 5 and subsequently, at first, the lamp light L is collected onto the tip-like second glass sheet S so that the lamp light 1 may be collected on an area the same as or slightly larger than that of the tip-like second glass sheet S. The luminous output is gradually increased to slowly raise the temperature of the whole tip-like second glass sheet S up to temperatures immediately lower than the melting temperature of the tip-like second glass sheet S (in the present preferred embodiment, about 600° C. lower than the softening point).

Then, the lamp light L having a comparatively higher luminous output (in the present preferred embodiment, about 1,200° C.) is additionally radiated onto the whole surface of the tip-like second glass sheet S for a short period of time (in the present preferred embodiment, about several seconds), while the sheet S is under the previously heated condition immediately before the melting, to add an appointed quantity of thermal energy to the tip-like second glass sheet S. Thereby, only the surface is uniformly melted as a whole and then solidified. Also, in this case, the simultaneous treatment of both the right side and the rear side of the tip-like second glass sheet S can be accomplished by radiating the lamp light L onto one surface side of the tip-like second glass sheet S. This lamp heat radiation method with previous heating is particularly suitable where the tip-like second glass sheet S is finely glassified all over the surface thereof. The method is also suitable where only a part (or desired place) of the tip-like second glass sheet S is finely glassified with a relatively small energy consumption, in the same manner as in the above described lamp heat radiation method with previous heating, by increasing the quantity of lamp heat collected after the previous heating, or radiating by scanning so the quantity of lamp heat collected is increased.

Another method (the third method) is "the belt transfer furnace method" (FIG. 9). It includes a rotating belt 11 moves in one direction at a designed speed within a furnace 10; a plurality of heaters 12 (in the present preferred embodiment, three up and down pairs), each adapted to be able to set a temperature separately from the other and provided along the belt-transferring direction of the furnace 10; and a controller 13 for controlling the rotating belt 11 and the heaters 12. A plurality of tip-like second glass sheets S obtained in the above described manner are formed as a working block 16 and put between two up and down substrates 14, 14, which are superior in heat conductivity, and through a super thin-spacer 15, 15 (FIG. 10). The substrates 14, 14 are, for example, a plate made of non-oxide ceramics, such as boron nitride and silicon nitride, a carbon plate, a carbon graphite plate, an alumina plate and the like. In the present preferred embodiment, an alumina plate of 50 mm deep, 50 mm wide, and 0.635 mm thick is used. In the present preferred embodiment, the spacer 15, 15 is an alumina plate 0.635 mm thick.

The plurality of working blocks 16 are placed on the rotating belt 11 in succession to pass through the furnace 10 within an appointed time (speed) toward an outlet 10B from an inlet 10A of the furnace 10. A relation between a transfer distance D and a temperature T of the working block 16 within the furnace 10 can be optionally designed by controlling a speed of the belt 11 by the controller 13 and controlling individual temperatures of the heaters 11, as schematically shown, for example, in FIG. 11. That is to say, the tip-like second glass sheet S in the working block 16 introduced into the furnace 10 through the inlet 10A of the furnace 10 is gradually heated during the previous heating period until coming to a point A (FIG. 11) so as to reach temperatures immediately below the melting temperature over all the sheet S (in the present preferred embodiment, about 600° C; in the case of a pHa-response glass membrane, about 700° C.). The sheet S further receives the appointed quantity of thermal energy within a remarkably short surface melting period (in the present preferred embodiment about 10 seconds) until a point B (FIG. 11), while under its previously heated condition immediately before the melting, whereby only the surface (both the right side and the rear side) is uniformly melted, and then it is cooled to a point C (cooling point) (FIG. 11) where it is solidified. Thus, the sheet S is subjected to high-speed surface heat treatment with previous heating.

In addition, referring to FIG. 9, reference numeral 10a designates a sprayer of air (or $N_2$ gas) for use in an inlet air curtain, and reference numeral 10b designates a sprayer of air (or $N_2$ gas) for use in firing gas and cooling gas which control temperature and humidity in the furnace 10. Thus, the temperature of the sheet 5 is controlled (FIG. 11). The gases also purge gases generated in the furnace 10. Reference numeral 10D designates an exhaust pipe of the firing gas and the cooling gas.

The above described belt transfer furnace method is particularly suitable where the tip-like second glass sheet S is finely glassified all over the surface thereof, and remarkably suitable for mass-production, as with the above described lamp heat radiation method with previous heating. A mass-production system can be constructed by also providing a handling system for automatically exchanging the tip-like second glass sheet S, or the heater block 2 for the laser heat radiation method (FIG. 7), or the working board 7 supporting the tip-like second glass sheet S for the lamp heat radiation method (FIG. 8), and the like.

In the case where the production of the second glass sheet by etching treatment is not required, the first glass sheet sliced by mechanically cutting is subjected to dieing to form tips and the resulting tip-like first glass sheet is subjected to the above described high-speed surface heat treatment under the previous heated condition in the same manner as said tip-like second glass sheet S.

As obvious from the above detailed description, a super-thin flat plate glass has never been realized. In short, a super-thin, flat plate glass, meets severe requirements including a sufficient thinness and size, no microcracking or strain is generated, crystallization (detransparency) being absent, the composition being uniform, a surface that is sufficiently flat and transparent, and can be easily and inexpensively manufactured regardless of the composition thereof. This is done by mechanically cutting (and additionally etching, if necessary) a glass block produced so as to have an appointed composition and then turned into a glass sheet. The glass sheet is subjected to a high-speed surface heating treatment after previous heating. Accordingly, a superior effect is exhibited in that a great contribution can be made to the manufacture of a glass responsive membrane (ion-responsive, super-thin, flat plate glass) required for a sheet type ion-measuring electrode which has been a great problem in the past. Furthermore, according to the present invention, a super-thin, flat-plate ion-response glass membrane, could not be produced until the present novel method of subjecting a flat, plate-like, super-thin glass, which has been formed to an appointed size, to a high-speed surface heat treatment under a previously heated condition. Also provided is a substrate and a support layer being formed of a material having a sufficiently high electrical insulating property, and the ion-response glass membrane is fixedly mounted on the support layer by the use of adhesives having a sufficiently high electrical insulating property, whereby superior effects can be exhibited in that a sheet type glass electrode having a desired high electrical insulating property can be produced very easily and inexpensively in comparison with the conventional glass electrode. As a result, the desired object of remarkably compacting and improving an ion-measuring glass electrode in reliability, operation, maintenance and the like can be achieved.

What is claimed is:

1. A sheet type glass electrode, comprising:
   a substrate formed of a material having an electrical insulating property;

an electrode provided with an internal electrode portion and a lead portion fixed to an upper surface of the substrate; and a support layer formed of a material having an electrical insulating property and describing a hole at a place corresponding to said internal electrode portion being formed on the upper surface of said substrate, whereby said lead portion and its circumference are exposed, said hole in the support layer being filled with a gelatinized internal solution, and a flat, plate-like ion-response glass membrane produced by subjecting a flat, plate-like glass, which has been previously formed with an appointed size, to a surface heating treatment with previous heating, is fixedly mounted on an upper surface of said support layer along a circumference thereof by the use of adhesives having an electrical insulating property so that a lower surface of said glass membrane may be stuck to an upper surface of said gelatinized internal solution and said hole may be filled with the gelatinized internal solution.

2. The invention of claim 1 wherein the substrate has a flat, planar configuration.

3. The invention of claim 2 wherein the support layer has a flat, planar configuration.

4. The invention of claim 3 wherein the internal electrode portion and the lead portion both have a flat, planar configuration.

5. The invention of claim 4 wherein the combined substrate, support layer, electrode, and glass membrane have a thickness of less than about 0.5 mm.

6. A sheet type composite electrode, comprising:

a flat, planar substrate made of an insulating material, the substrate having a central portion and an end portion;

a pair of flat outside electrodes fixed on the substrate, the outside electrodes each having an internal electrode portion positioned in the central portion of the substrate and also having a first lead portion extending to the end portion of the substrate;

a pair of flat inside electrodes fixed on the substrate;

a flat temperature-compensating electrode portion fixed between two ends of the inside electrodes;

a support layer made of an insulating material and defining a pair of holes that overlay the two internal electrode portions of the outside electrodes, and when so overlaid, the internal electrode portions interface a lower surface of the support layer, and also the end portion and the first lead portion remain exposed;

a pair of gelatinized internal solutions, one being disposed in each of the holes in the support layer;

a flat, plate-like ion-responsive glass membrane positioned across one hole and adhered on an upper surface of the support layer; and a flat, plate-like liquid junction membrane positioned across the other hole and adhered on an upper surface of the support layer.

7. The invention of claim 6 wherein the inside electrodes are positioned between and generally parallel to the outside electrodes.

8. The invention of claim 7 wherein the inside electrodes have a second lead portion that extends to the end portion and remains exposed.

9. The invention of claim 8 wherein the ion-response glass membrane and the liquid junction membrane contact a respective internal solution.

10. In a sheet type composite electrode having a flat, insulating substrate; two pairs of flat electrodes on the substrate; and a flat, insulating support layer that overlays the substrate and the electrodes which describes at least a first and a second hole that expose portions of the electrodes to an internal solution, an improved membrane system, comprising:

an ion response membrane stationarily mounted on the support layer and positioned across the first hole to contact the internal solution, the ion response membrane having a flat, plate-like configuration and being constructed by producing a glass sheet with an aimed thickness, heating the glass sheet up to a temperature immediately below its melting temperature, and then adding an additional appointed quantity of thermal energy to the glass sheet, whereby only the surface of the glass sheet is melted and then solidified.

11. The invention of claim 10 wherein the glass sheet is optionally subjected to an etching treatment.

12. The improvement of claim 11 wherein the ion-response membrane is constructed by the further step of providing a glass block from which the glass sheet can be cut.

13. The invention of claim 12 wherein the glass sheet is heated by one of a laser heat radiation method, a lamp heat radiation method, and a belt transfer furnace method.

14. The improvement of claim 13 further comprising a flat, plate-like liquid junction membrane mounted on the support layer and positioned across the second hole.

* * * * *